US012150751B2

(12) United States Patent
Govari et al.

(10) Patent No.: US 12,150,751 B2
(45) Date of Patent: *Nov. 26, 2024

(54) CATHETER SPLINES WITH EMBEDDED CIRCUIT ELEMENTS

(71) Applicant: Biosense Webster (Israel) Ltd., Yokneam (IL)

(72) Inventors: Assaf Govari, Haifa (IL); Andres Claudio Altmann, Haifa (IL); Christopher Thomas Beeckler, Brea, CA (US); Joseph Thomas Keyes, Glendora, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 592 days.

This patent is subject to a terminal disclaimer.

(21) Appl. No.: 17/145,449

(22) Filed: Jan. 11, 2021

(65) Prior Publication Data

US 2021/0128010 A1 May 6, 2021

Related U.S. Application Data

(62) Division of application No. 15/376,807, filed on Dec. 13, 2016, now Pat. No. 10,918,306.

(51) Int. Cl.
*A61B 5/00* (2006.01)
*A61B 5/05* (2021.01)
(Continued)

(52) U.S. Cl.
CPC .............. *A61B 5/062* (2013.01); *A61B 5/287* (2021.01); *A61B 5/6858* (2013.01);
(Continued)

(58) Field of Classification Search
CPC .... A61B 2018/1407; A61B 2018/1435; A61B 2018/1437; A61B 8/0841; A61B 18/1492;
(Continued)

(56) References Cited

U.S. PATENT DOCUMENTS 5,391,199 A   2/1995   Ben-Haim
5,800,494 A   9/1998   Campbell et al.
(Continued)

FOREIGN PATENT DOCUMENTS

CN   104644162 A   5/2015
CN   105796090 A   7/2016
(Continued)

OTHER PUBLICATIONS

Peters, Christian, and Yiannos Manoli. "Inductance calculation of planar multi-layer and multi-wire coils: An analytical approach." *Sensors and Actuators A: Physical* 145 (2008): 394-404.
(Continued)

*Primary Examiner* — Joseph A Stoklosa
*Assistant Examiner* — Brian M Antiskay
(74) *Attorney, Agent, or Firm* — Frost Brown Todd LLP

(57) ABSTRACT

Medical apparatus includes one or more magnetic field generators, which are configured to generate magnetic fields within a body of a patient. An invasive probe includes an insertion tube having a distal end, which is configured for insertion into the body, and a plurality of flexible splines configured to be deployed from the distal end of the insertion tube. Each spline includes a flexible, multilayer circuit board and a conductive trace that is formed in at least one layer of the circuit board and is configured to define one or more coils, which are disposed along a length of the spline and output electrical signals in response to the magnetic fields. A processor is coupled to receive and process the electrical signals output by the coils in order to derive respective positions of the flexible splines in the body.

20 Claims, 4 Drawing Sheets

(51) Int. Cl.

| | | |
|---|---|---|
| *A61B 5/06* | (2006.01) | |
| *A61B 5/287* | (2021.01) | |
| *A61B 8/08* | (2006.01) | |
| *A61B 18/00* | (2006.01) | |
| *A61B 18/14* | (2006.01) | |
| *H05K 1/02* | (2006.01) | |
| *H05K 1/11* | (2006.01) | |
| *H05K 1/16* | (2006.01) | |
| *H05K 3/00* | (2006.01) | |
| *H05K 3/46* | (2006.01) | |
| *A61B 17/00* | (2006.01) | |
| *A61B 34/20* | (2016.01) | |

(52) U.S. Cl.
CPC .......... *A61B 5/6859* (2013.01); *A61B 5/6886* (2013.01); *A61B 8/0841* (2013.01); *A61B 18/1492* (2013.01); *H05K 1/028* (2013.01); *H05K 1/11* (2013.01); *H05K 1/165* (2013.01); *H05K 3/0044* (2013.01); *H05K 3/4644* (2013.01); *A61B 2017/0011* (2013.01); *A61B 2018/00077* (2013.01); *A61B 2018/00267* (2013.01); *A61B 2018/00351* (2013.01); *A61B 2018/00577* (2013.01); *A61B 2018/00642* (2013.01); *A61B 2018/00839* (2013.01); *A61B 2018/00875* (2013.01); *A61B 2018/00988* (2013.01); *A61B 2034/2051* (2016.02); *A61B 2562/0204* (2013.01); *A61B 2562/0209* (2013.01); *A61B 2562/0223* (2013.01); *A61B 2562/125* (2013.01); *H05K 2201/10151* (2013.01)

(58) Field of Classification Search
CPC ... A61B 5/0422; A61B 5/6886; A61B 5/6859; A61B 5/6858; A61B 2090/061; A61B 2017/0011; A61B 2034/2051; A61B 2562/0223; A61B 2562/0204; A61B 2562/0209; A61B 2562/125; A61B 2018/00988; A61B 2018/00267; A61B 2018/00351; A61B 2018/00577; A61B 2018/00642; A61B 2018/00839; A61B 2018/00875; A61B 2018/00077; H05K 1/11; H05K 1/165; H05K 1/028; H05K 3/0044; H05K 3/4644; H05K 2201/10151
USPC ........ 600/372, 374, 407–409, 424, 508–509; 606/20–42
See application file for complete search history.

(56) References Cited

U.S. PATENT DOCUMENTS

| | | |
|---|---|---|
| 5,928,228 A | 7/1999 | Kordis et al. |
| 6,073,043 A | 6/2000 | Schneider |
| 6,201,387 B1 | 3/2001 | Govari |
| 6,239,724 B1 | 5/2001 | Doron et al. |
| 6,332,089 B1 | 12/2001 | Acker et al. |
| 6,484,118 B1 | 11/2002 | Govari |
| 6,529,756 B1 | 3/2003 | Phan et al. |
| 6,618,612 B1 | 9/2003 | Acker et al. |
| 6,690,963 B2 | 2/2004 | Ben-Haim et al. |
| 6,748,255 B2 | 6/2004 | Fuimaono et al. |
| 10,918,306 B2 | 2/2021 | Govari et al. |
| 2002/0055674 A1 | 5/2002 | Ben-Haim et al. |
| 2002/0065455 A1 | 5/2002 | Ben-Haim et al. |
| 2003/0078509 A1 | 4/2003 | Panescu |
| 2003/0120150 A1 | 6/2003 | Govari |
| 2003/0176816 A1 | 9/2003 | Maguire et al. |
| 2003/0187347 A1 | 10/2003 | Nevo et al. |
| 2003/0233099 A1 | 12/2003 | Danaek et al. |
| 2004/0068178 A1 | 4/2004 | Govari |
| 2006/0000969 A1 | 1/2006 | Sano |
| 2012/0143298 A1 | 6/2012 | Just et al. |
| 2013/0066194 A1 | 3/2013 | Seter et al. |
| 2014/0276004 A1 | 9/2014 | Strupeck et al. |
| 2014/0350553 A1 | 11/2014 | Okuyama |
| 2015/0196354 A1 | 7/2015 | Haverkost et al. |
| 2015/0250424 A1 | 9/2015 | Govari et al. |
| 2015/0366508 A1 | 12/2015 | Chou et al. |
| 2016/0135882 A1 | 5/2016 | Weinkam et al. |
| 2016/0324474 A1 | 11/2016 | Sterrett et al. |
| 2018/0317313 A1 | 11/2018 | Kegeler |
| 2019/0223758 A1 | 7/2019 | Just |

FOREIGN PATENT DOCUMENTS

| | | |
|---|---|---|
| WO | WO 1996/005768 A1 | 2/1996 |
| WO | WO 2014/036439 A2 | 3/2014 |

OTHER PUBLICATIONS

Extended European Search Report dated May 22, 2018, for Application No. 17206730.8, 9 pages.
Chinese Office Action and Search Report dated Sep. 23, 2021, for Application No. 201711334420.3, 13 pages.
European Communication dated Apr. 21, 2021, for Application No. 17206730.8, 8 pages.
Japanese Notification of Reasons for Refusal dated Oct. 5, 2021, for Application No. 2017-237434, 3 pages.

CATHETER SPLINES WITH EMBEDDED CIRCUIT ELEMENTS

FIELD OF THE INVENTION

The present invention relates generally to invasive medical devices, and particularly to catheters having multiple distal splines.

BACKGROUND

Some types of catheters have multiple elongate flexible segments joined together to the distal end of the catheter. These segments, which are commonly referred to as "splines," may have the form of separate arms, for example, which are joined at their proximal extremities to the catheter and open out in different directions, as in the PentaRay® catheter produced by Biosense Webster, Inc. (Diamond Bar, California). Alternatively, the splines may be configured as staves of a basket, which are joined together at both their proximal and distal extremities. In cardiac electrophysiology applications, multiple sensing electrodes are attached to the splines, and are used to simultaneously measure electrical signals at multiple locations in the heart.

For example, U.S. Pat. No. 6,748,255, whose disclosure is incorporated herein by reference, describes a basket catheter for mapping the heart. The catheter comprises an elongated catheter body and at least one lumen therethrough. A basket-shaped electrode assembly is mounted at the distal end of the catheter body. The basket assembly comprises a plurality of splines connected at their proximal and distal ends. Each spline comprises at least one electrode. The basket assembly has an expanded arrangement wherein the splines bow radially outwardly and a collapsed arrangement wherein the splines are arranged generally along the axis of the catheter body.

The catheter further comprises a distal location sensor mounted at or near the distal end of the basket-shaped electrode assembly and a proximal location sensor mounted at or near the proximal end of the basket-shaped electrode assembly. In use, the coordinates of the distal location sensor relative to those of the proximal sensor can be determined and taken together with known information pertaining to the curvature of the splines of the basket-shaped mapping assembly to find the positions of the at least one electrode of each spline.

As another example, U.S. Patent Application Publication 2015/0366508, issued as U.S. Pat. No. 10,201,311 on Feb. 12, 2019, describes a flex-PCB catheter device that is configured to be inserted into a body lumen. The flex-PCB catheter comprises an elongate shaft, an expandable assembly, a flexible printed circuit board (flex-PCB) substrate, a plurality of electronic components and a plurality of communication paths. The expandable assembly is configured to transition from a radially compact state to a radially expanded state. The plurality of electronic elements are coupled to the flex-PCB substrate and are configured to receive and/or transmit an electric signal. The plurality of communication paths are positioned on and/or within the flex-PCB substrate and selectively couple the plurality of electronic elements to a plurality of electrical contacts configured to electrically connect to an electronic module configured to process the electrical signal. The flex-PCB substrate can have multiple layers, including one or more metallic layers. Acoustic matching elements and conductive traces can be included in the flex-PCB substrate.

SUMMARY

Embodiments of the present invention that are described hereinbelow provide improved multi-spline probes, as well as methods associated with such probes.

There is therefore provided, in accordance with an embodiment of the invention, medical apparatus, including one or more magnetic field generators, which are configured to generate magnetic fields within a body of a patient. An invasive probe includes an insertion tube having a distal end, which is configured for insertion into the body, and a plurality of flexible splines configured to be deployed from the distal end of the insertion tube. Each spline includes a flexible, multilayer circuit board and a conductive trace that is formed in at least one layer of the circuit board and is configured to define one or more coils, which are disposed along a length of the spline and output electrical signals in response to the magnetic fields. A processor is coupled to receive and process the electrical signals output by the coils in order to derive respective positions of the flexible splines in the body.

In some embodiments, the flexible splines have respective distal and proximal extremities and are connected together at both the distal and proximal extremities to define a basket assembly, which has a collapsed configuration, in which the splines are held parallel to the insertion tube during insertion into the body, and an expanded configuration, in which the splines bow radially outward within a cavity in the body. In one embodiment, the flexible, multilayer circuit board has a resilience sufficient to cause the splines to bow radially outward within the cavity.

Typically, the multilayer circuit board includes further conductive traces, which are connected to the one or more coils and run along the length of the splines so as to couple the electrical signals to the processor.

Additionally or alternatively, the multilayer circuit board includes electrodes, which are disposed on an outer surface of each spline so as contact tissue at respective locations within the body. The processor may be configured to map electrical activity in the body responsively to the electrical activity sensed by the electrodes and the positions of the flexible splines that are derived from the signals output by the coils.

Further additionally or alternatively, the invasive probe includes acoustic transducers that are fixed to the multilayer circuit board on one or more of the flexible splines, wherein the multilayer circuit board includes further conductive traces, which are connected to the acoustic transducers and run along the length of the splines so as to couple the acoustic transducers to the processor.

In a disclosed embodiment, the one or more coils include multiple coils disposed along the length of each of the splines, and the processor is configured to derive both locations and orientations of the splines from the electrical signals output by the coils.

There is also provided, in accordance with an embodiment of the invention, a method for medical diagnosis or treatment. The method includes generating magnetic fields within a body of a patient and inserting a distal end of an insertion tube into the body. A plurality of flexible splines are deployed from the distal end of the insertion tube into the body. Each spline includes a flexible, multilayer circuit board and a conductive trace that is formed in at least one layer of the circuit board and is configured to define one or more coils, which are disposed along a length of the spline and output electrical signals in response to the magnetic fields. The electrical signals output by the coils are processed in order to derive respective positions of the flexible splines in the body.

There is additionally provided, in accordance with an embodiment of the invention, a method for producing an invasive probe, which includes providing an insertion tube having a distal end, which is configured for insertion into the body. Multiple, successive layers of metal traces and dielectric material are deposited on a flexible polymer substrate to produce a flexible printed circuit board, including a conductive trace that is formed in at least one of the layers and is configured to define multiple coils. The flexible printed circuit board is sliced into a plurality of ribbons, which are deployed as flexible splines extending from the distal end of the insertion tube.

The present invention will be more fully understood from the following detailed description of the embodiments thereof, taken together with the drawings in which:

DETAILED DESCRIPTION OF EMBODIMENTS

Figure 1:
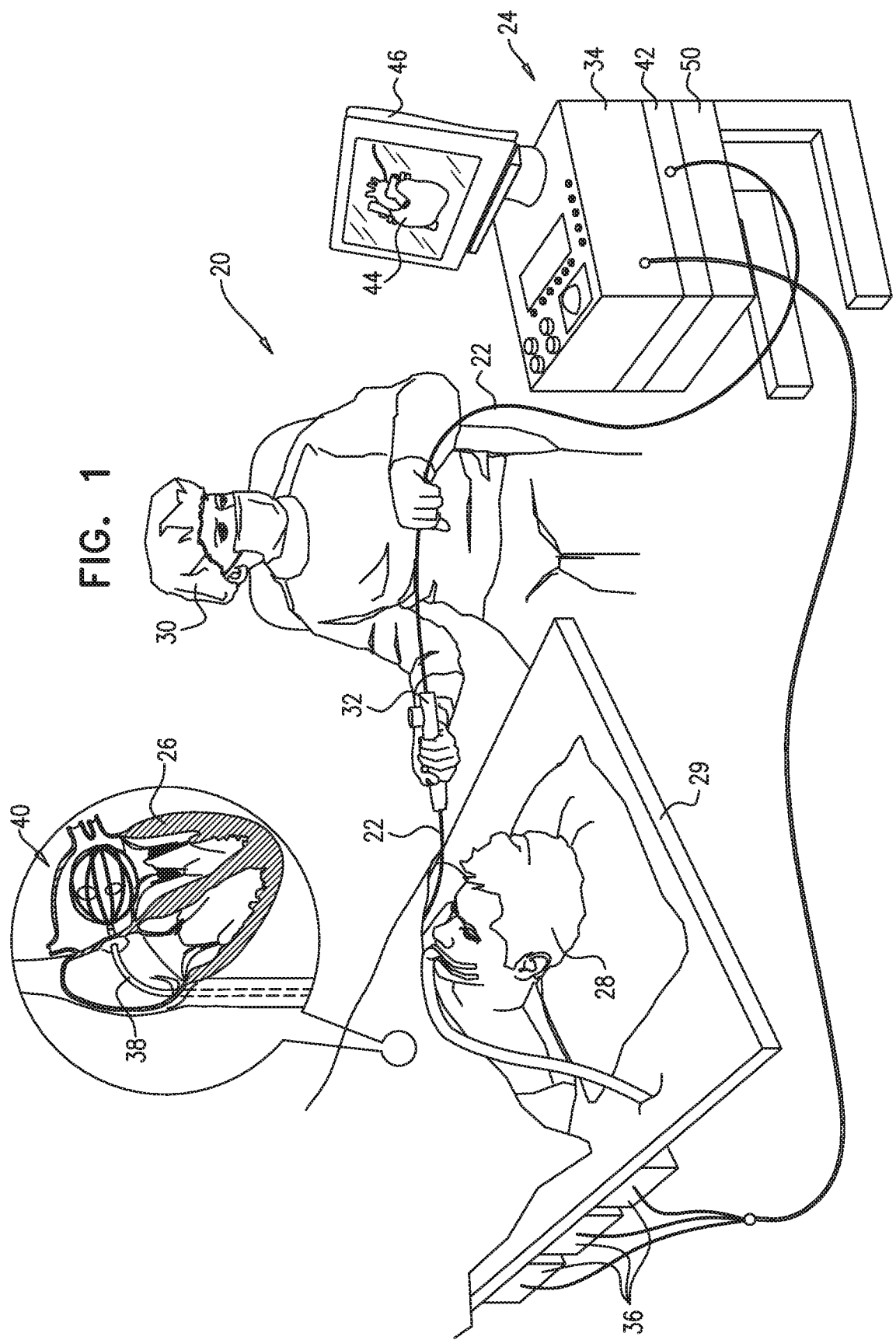
FIG. 1 is schematic pictorial illustration of a system for cardiac catheterization, in accordance with an embodiment of the invention.

Multi-spline catheters, such as basket catheters and multi-arm catheters, are useful in both diagnostic and therapeutic applications. For precise mapping and treatment, it is important that the splines be accurately tracked and positioned within the heart. For this purpose, discrete magnetic sensors may be fixed to the splines. Such sensors typically comprise wire-wound coils, although solid-state devices, such as Hall Effect sensors, are sometimes used. The electrical signals output by the sensors in response to magnetic fields generated in the body can give accurate indications of the locations and orientations of the splines. To accurately track all the splines, however, a large number of sensors is needed, which can make such catheters prohibitively difficult and expensive to manufacture.

Multi-spline catheters can efficiently be made from ribbons of flexible printed circuit board material. In this sort of implementation, the circuit board typically comprises electrodes, which are disposed on the outer surface of each spline so as contact tissue at respective locations within the body. If the locations and orientations of the splines are accurately known, the outputs of the electrodes can be used in mapping electrical activity in the body (particularly within chambers of the heart). Additionally or alternatively, the electrodes may be driven with electrical current in order to ablate the tissue.

Embodiments of the present invention that are described herein provide invasive medical probes having multiple distal splines that are made from ribbons of flexible printed circuit board, and take advantage of this structure in order sense spline positions magnetically, while avoiding the need for discrete field sensors. In the disclosed embodiments, an invasive probe, such as a catheter, comprises an insertion tube, whose distal end is inserted into the body, with flexible splines of this sort deployed from the distal end (for example, in a basket or multi-arm configuration). A conductive trace is formed in at least one layer of the circuit board so as to define one or more coils that are disposed along the length of each spline. One or more magnetic field generators generate magnetic fields within the body of a patient into which the probe is inserted. The electrical signals that are output by the coils in response to these magnetic fields can then be processed in order to derive respective positions of the flexible splines in the body. Since the coils are integrated into the printed circuit ribbons, they are robust and add only negligible manufacturing cost to the probe.

For the sake of clarity and concreteness of illustration, the embodiments described below relate specifically to a basket catheter for deployment inside the heart. The principles of the present invention, however, are not limited to this specific sort of catheter, but may rather be applied to other types of multi-spline catheters, such as multi-arm catheters, as well as to multi-spline probes for use in other body cavities and organs.

FIG. 1 is a schematic, pictorial illustration of a system 20 for cardiac catheterization, in accordance with an embodiment of the present invention. System 20 comprises a catheter 22, which is connected at its proximal end to a control console 24. In the embodiment described herein, catheter 22 may be used for any suitable therapeutic and/or diagnostic purposes, such as ablation of tissue in a heart 26 of a patient 28 and/or mapping of electrophysiological signals for the diagnosis of cardiac pathologies, such as cardiac arrhythmias, for example.

An operator 30 (such as an interventional cardiologist) inserts catheter 22 through the vascular system of patient 28, who is shown lying on a table 29. Catheter 22 comprises an insertion tube 38 with a basket assembly 40 deployed from its distal end, as shown in the figures that follow. Operator 30 advances insertion tube 38 through the vascular system of patient 28 until assembly 40 is located in a desired chamber of heart 26, typically by manipulating a handle 32 connected to the proximal end of the insertion tube. The proximal end of catheter 22 is connected by a cable to interface circuitry 42 in console 24.

Console 24 tracks the locations and orientations of the splines of basket assembly 40 within heart 26 by magnetic position sensing. For this purpose, console 24 comprises a driver circuit 34, which drives magnetic field generators 36 that are placed at known positions external to the body of patient 28, in this case on or below table 29. Basket assembly 40 comprises multiple coils, which are disposed along the lengths of the splines of the basket assembly (as shown in the figures that follow) and output electrical signals in response to the magnetic fields.

Interface circuitry 42 amplifies and digitizes these electrical signals and passes the digital signal values to a processor 50 in console 24. Typically, processor 50 comprises a general-purpose microprocessor, which is programmed in software to process the signals output by the coils in order to derive respective positions of the flexible splines in the body. Additionally or alternatively, at least some of the functions of processor 50 may be implemented in hard-wired or programmable logic. Processor 50 converts the electrical signals to location and orientation coordinates using methods that are implemented, for example, in the CARTO™ system, produced by Biosense Webster, Inc. Such methods are described in detail, for example, in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455, issued as U.S. Pat. No. 6,690,963 on Feb. 10, 2004, 2003/0120150, issued as U.S. Pat. No. 7,729,742 on Jun. 1, 2010 and 2004/0068178, now abandoned, whose disclosures are all incorporated herein by reference. In some embodiments, processor 50 overlays the positions of the splines in basket assembly 40 on a map 44 or other image of heart 26, which is presented on a display screen 46.

Figure 2:
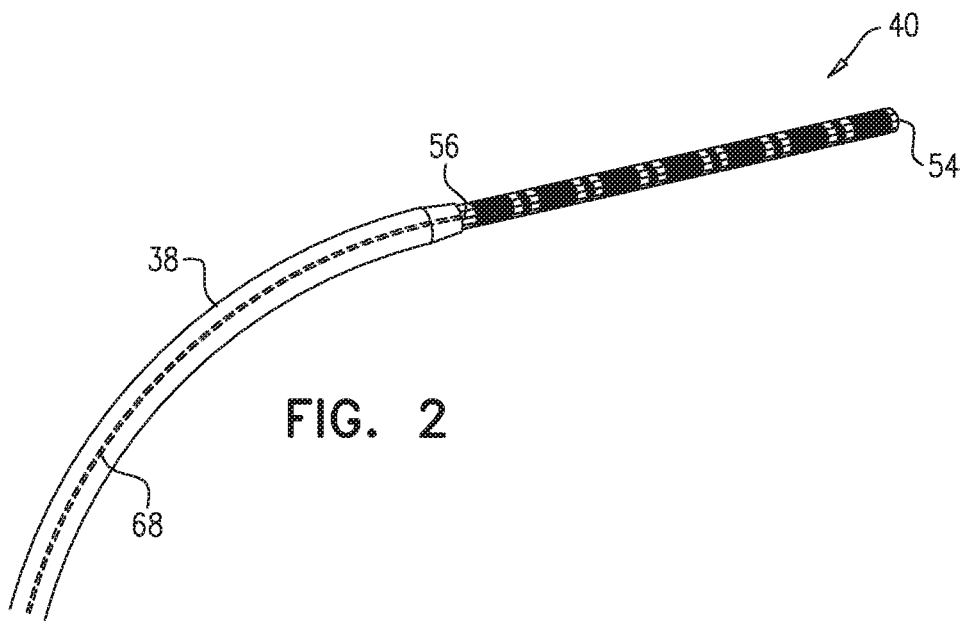
FIGS. 2 and 3 are schematic pictorial illustrations of a basket assembly at the distal end of a catheter in collapsed and expanded configurations, respectively, in accordance with an embodiment of the invention.
Figure 3:
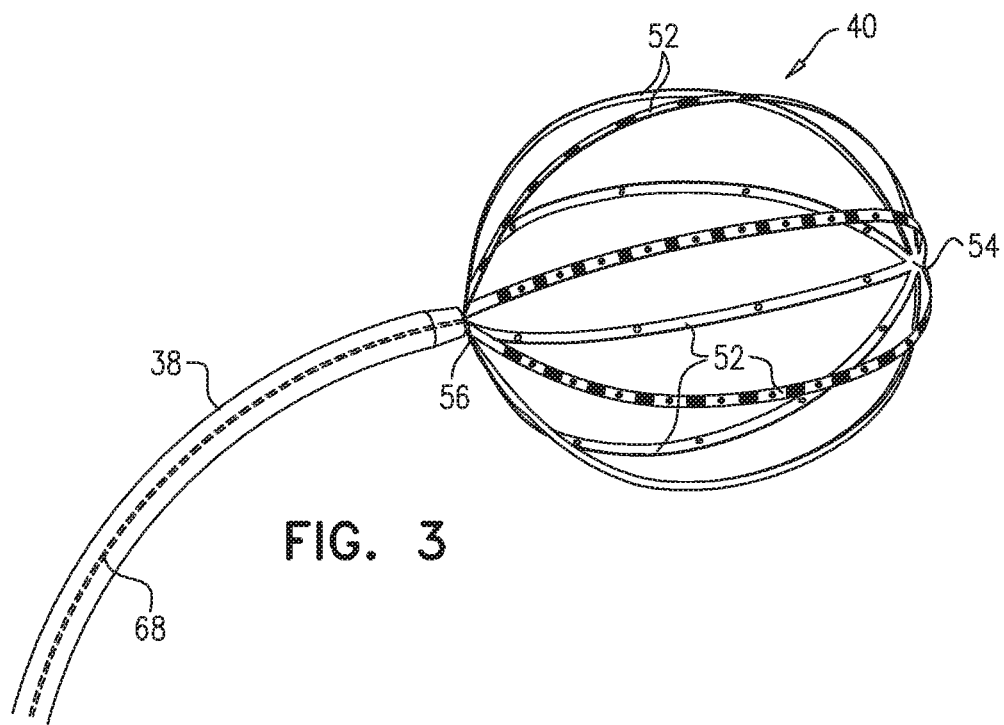

FIGS. 2 and 3 are schematic pictorial illustrations of basket assembly 40 at the distal end of insertion tube 38, in collapsed and expanded configurations, respectively, in accordance with an embodiment of the invention. Assembly 40 comprises multiple splines 52, which are shown in greater detail in FIGS. 4A/B. Splines 52 are connected together at both their distal extremities 54 and proximal extremities 56 to define basket assembly 40. In the collapsed configuration, shown in FIG. 2, splines 52 are held parallel to insertion tube 38 during insertion into the body. In the expanded configuration, shown in FIG. 3, splines 52 bow radially outward within a cavity in the body, such as in the left atrium of heart 26 as shown in FIGS. 1 and 5. Operator 30 is able to change the configuration of basket assembly 40 as desired, for example using suitable controls on handle 32.

Figure 4A:
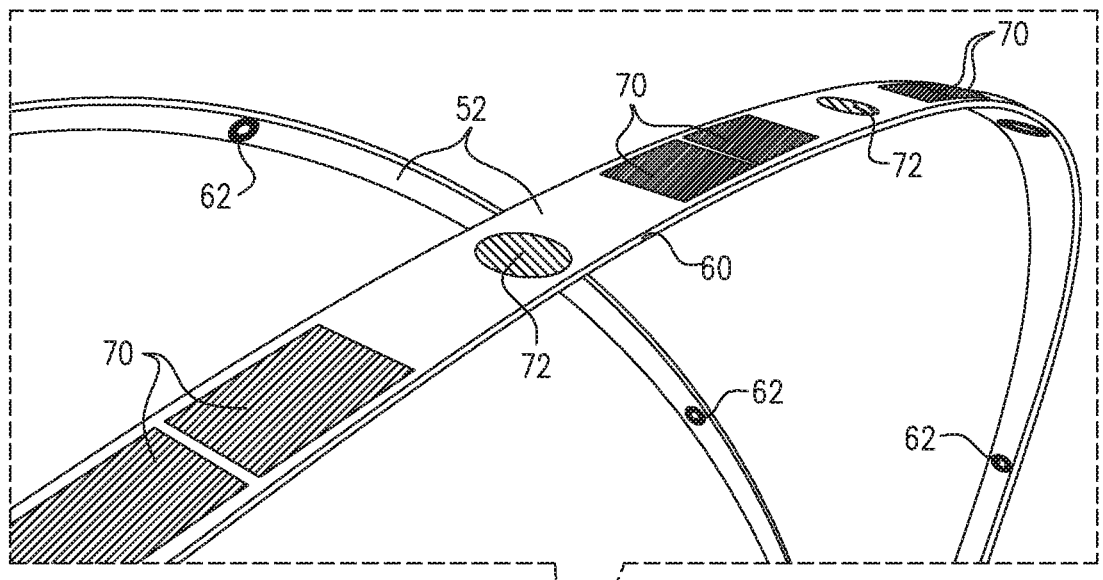
FIGS. 4A and 4B are schematic, detail views of structures on the splines of the basket assembly shown in FIG. 3, in accordance with an embodiment of the invention.
Figure 4B:
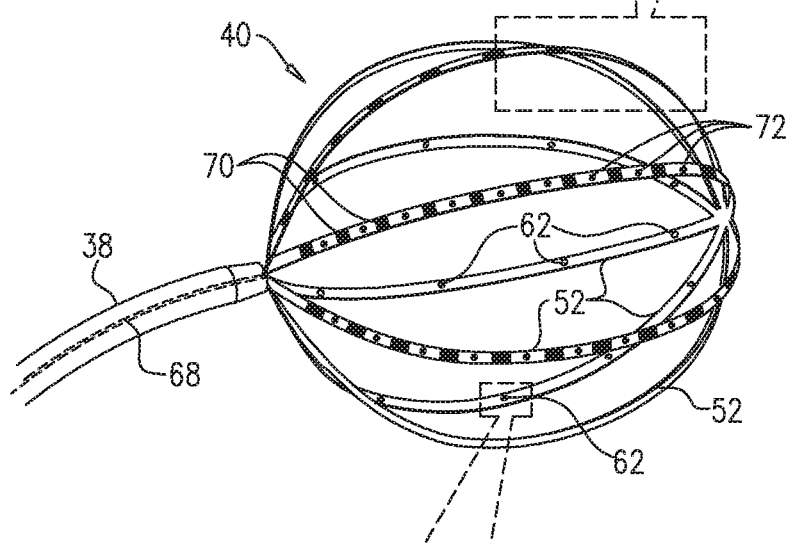
Figure 4B:
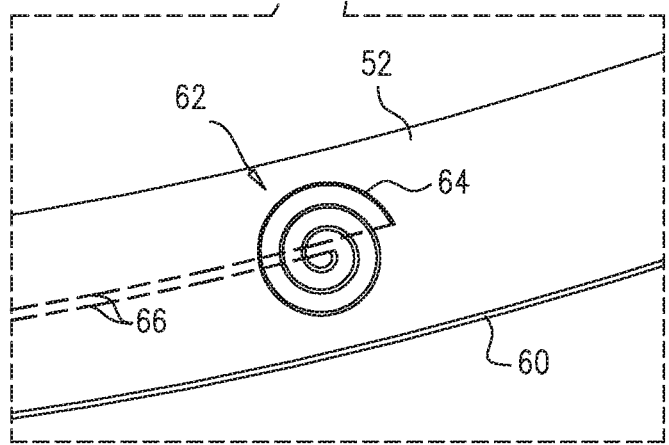
Figure 5:
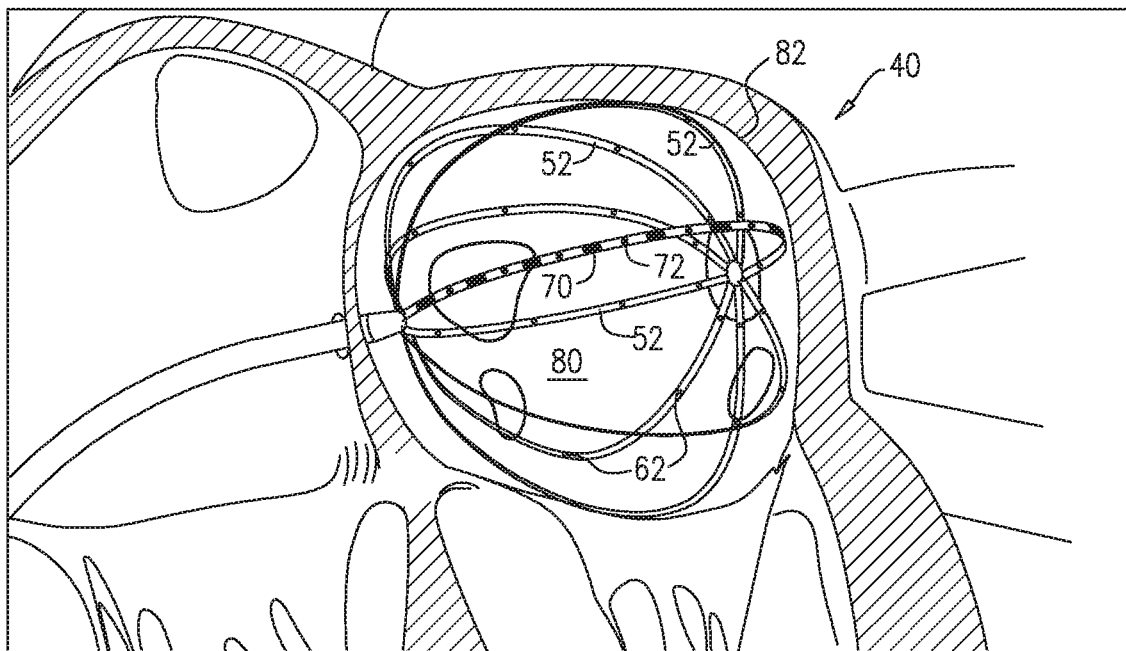
FIG. 5 is a schematic pictorial illustration of the basket assembly of FIGS. 2 and 3 when deployed in a chamber of a heart, in accordance with an embodiment of the invention.

FIGS. 4A and 4B are schematic, detail views of structures on splines 52 of basket assembly 40, in accordance with an embodiment of the invention. Each spline 52 comprises a ribbon of flexible, multilayer circuit board 60, thus forming an arm that is flexible about its longitudinal axis. Flexible circuit board 60 typically comprises a suitable polymer substrate, such as polyimide (which is sold under the trade name Kapton™), or from any other suitable material that allows for bending between the collapsed and expanded configurations. Typically, the circuit structures on board 60 include multiple, successive layers of metal traces and dielectric material deposited on the substrate, with vias interconnecting the metal traces in different layers, as is known in the art. For ease of manufacturing, the structures on multiple ribbons may be fabricated side-by-side on a single substrate and then sliced apart (using laser cutting, for example) to separate the ribbons.

In some embodiments, circuit board 60 has a resilience sufficient to cause splines 52 to bow radially outward when released (within a cavity such as a heart chamber, for example). In this case, there is no need for any additional strengthening member, such as a metal or plastic filament, along the splines. Alternatively, a strengthening element may be coupled along circuit board 60 in order to mechanically strengthen the spline.

Circuit board 60 comprises coils 62, which are disposed along the length of each spline 52 and output electrical signals in response to the magnetic fields applied by field generators 36. Each coil 62 comprises a conductive trace 64 that is formed in at least one layer of circuit board 60. Multi-level coils, with increased inductance, may be formed by interconnecting loops of traces 64 in different layers of circuit board 60 by vias running between the layers. Further conductive traces 66 are connected to conductive trace 64 of coil 62 and run along the lengths of splines 52 to connect with conductors 68 running through insertion tube, and thus couple the electrical signals from the coils via interface circuitry 42 to processor 50 in console 24. Processor 50 digitally processes these signals, explained above, in order to derive respective location and orientation coordinates of coils 62, and thus find the positions of the splines 52 in which the coils are embedded.

In the pictured embodiment, circuit board 60 also comprises embedded electrodes 70, which are disposed on the outer surface of splines 52 so as contact tissue at respective locations within the body when basket assembly 40 is expanded. Electrodes 70 thus output signals in response to electrical activity in the tissue, and these signals are conveyed via additional conductive traces (not shown) on or in circuit board 60 and conductors 68 to processor 50. The processor is then able to map electrical activity in the body based on the electrical activity sensed by electrodes 70 and the positions of the flexible splines 52 that are derived from the signals output by coils 62. Additionally or alternatively, console 24 may drive electrodes 70 with high-power radio-frequency (RF) currents in order to ablate tissue in heart 26 with which the electrodes are in contact.

As another option, additionally or alternatively, acoustic transducers 72, such as miniature piezoelectric crystals, can be fixed to circuit board 60 on one or more of splines 52. Circuit board 60 comprises further conductive traces (not shown), which are connected to acoustic transducers 72 and run along the length of splines 52 and connect to conductors 68 so as to couple the transducers to console 24. Typically, console 24 drives transducers 72 to transmit and receive ultrasound beams in A-mode. In this mode, processor 50 measures the time of flight of the ultrasound waves that are reflected from the heart wall back to each transducer 72. This measurement can give an indication of the electrode-tissue distance and/or the thickness of the heart wall at the location of the transducer.

FIG. 5 is a schematic pictorial illustration of the basket assembly of FIGS. 2 and 3 when deployed in the expanded configuration in a left atrium 80 of heart 26, in accordance with an embodiment of the invention. Splines 52 bow resiliently outward, while operator 30 (FIG. 1) exerts forward pressure so that the splines engage an inner wall 82 of atrium 80 along substantial portions of their lengths. Coils 62 output signals that enable processor 50 to derive the positions of splines 52 and possibly to display these positions on screen 46.

The signals output by acoustic transducers 72 give an indication as to the locations where splines 52 are in close contact with wall 82. Alternatively or additionally, processor 50 may evaluate the quality of contact by measuring the impedance between each of electrodes 70 and the tissue of wall 82, as is known in the art. Further additionally or alternatively, based on the electrical activity sensed by electrodes 70 that are in contact with the tissue of wall 82 and the coordinates of coils 62, processor 50 constructs map 44 showing topographical features of atrium 80 and the distribution of electrical activity relative to these topographical features.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for producing an invasive probe, comprising:
   (a) providing an insertion tube with a distal end, which is configured for insertion into a body;

(b) depositing multiple, successive layers of metal traces and dielectric material on a flexible polymer substrate to produce a flexible printed circuit board, including a conductive trace that is formed in at least one of the layers and is configured to define one or more coils, the flexible printed circuit board configured with an outward facing surface and an inward facing surface;

(c) coupling electrodes to the flexible printed circuit board, the electrodes being disposed on the outward facing surface such that the electrodes are configured for contact with body tissue at respective locations within the body;

(d) providing each of the one or more coils on the inward facing surface of the flexible printed circuit board such that the coils are not configured for contact with the body tissue when the electrodes disposed on the outward facing surface are in contact with the body tissue; and (e) separating the flexible printed circuit board into a plurality of ribbons configured to be deployed as flexible splines from the distal end of the insertion tube, each flexible spline including at least one of the electrodes and one of the coils.

2. The method of claim 1, the flexible splines configured with respective distal and proximal extremities, the method further comprising connecting the splines together at both the distal and proximal extremities to define a basket assembly.

3. The method of claim 1, further comprising connecting the flexible splines together at both the distal and proximal extremities to bow the flexible splines radially outward within a cavity in the body upon being deployed.

4. The method of claim 3, further comprising providing the flexible printed circuit board with a resilience sufficient to cause the flexible splines to bow radially outward within the cavity.

5. The method of claim 1, further comprising activating a laser cutting device configured to separate the flexible printed circuit board into the plurality of ribbons.

6. The method of claim 1, further comprising coupling a processor with the coils.

7. A method for producing an invasive probe, comprising:
(a) providing an insertion tube having a distal end, which is configured for insertion into a body;
(b) depositing multiple, successive layers of metal traces and dielectric material on a flexible polymer substrate to produce a flexible printed circuit board, including a conductive trace that is formed in at least one of the layers and is configured to define one or more coils;
(c) coupling electrodes to the flexible printed circuit board, the electrodes being disposed on an outward facing surface such that the electrodes are configured for contact with body tissue at respective locations within the body;
(d) providing each of the one or more coils on an inward facing surface of the flexible printed circuit board such that the coils are not configured for contact with the body tissue when the electrodes disposed on the outward facing surface are in contact with the body tissue;
(e) separating the flexible printed circuit board into a plurality of ribbons;
(f) forming the plurality of ribbons as flexible splines extending from the distal end of the insertion tube, the flexible splines having respective distal and proximal extremities; and (g) connecting the flexible splines together at both the distal and proximal extremities to define a basket assembly.

8. The method of claim 7, further comprising activating a laser cutting device for separating the flexible printed circuit board into the plurality of ribbons.

9. The method of claim 7, further comprising coupling the one or more coils to a processor via the conductive trace, the conductive trace configured to transfer electrical signals from the one or more coils to the processor.

10. The method of claim 1, further comprising affixing an acoustic transducer to one of the splines.

11. The method of claim 10, the acoustic transducer includes a miniature piezoelectric crystal.

12. The method of claim 1, the electrodes are configured to output signals in response to electrical activity in the body tissue.

13. The method of claim 1, the electrodes are configured to ablate the body tissue.

14. The method of claim 1, the one or more coils include multi-level coils comprising loops of traces in different layers of the flexible printed circuit board interconnected by vias running between the layers.

15. The method of claim 1, the coils are responsive to magnetic fields.

16. The method of claim 1, further comprising forming vias running between the layers of the flexible printed circuit board connecting the metal traces.

17. A method for producing an invasive probe, comprising:
(a) providing an insertion tube with a distal end, which is configured for insertion into a body;
(b) depositing metal traces and dielectric material on a flexible polymer substrate to produce a flexible printed circuit board with first and second surfaces, the metal traces including conductive traces and coils;
(c) coupling electrodes to the flexible printed circuit board, the electrodes being disposed on the first surface;
(d) forming the coils on the second surface of the flexible printed circuit board, the flexible printed circuit board configured with the electrodes and the coils for separation into a plurality of ribbons in a side-by-side configuration with the electrodes on an outward facing surface of the ribbons and the coils on an inward facing surface of the ribbons; and
(e) separating the plurality of ribbons from each other such that each ribbon is configured to be deployed as a flexible spline, each flexible spline including at least one of the electrodes and one of the coils, the electrodes on the outward facing surface of the ribbons are configured for contact with body tissue at respective locations within the body and the coils on the inward facing surface of the ribbons are not configured for contact with the body tissue when the electrodes are in contact with the body tissue.

18. The method of claim 17, further comprising affixing acoustic transducers on the first surface of the flexible printed circuit board.

19. The method of claim 17, the coils are configured to be responsive to a magnetic field.

20. The method of claim 17, the electrodes are configured to be responsive to electrical activity in the body tissue.

* * * * *